(12) United States Patent
Kenney

(10) Patent No.: US 8,151,478 B2
(45) Date of Patent: Apr. 10, 2012

(54) GENERAL MEASURING SYSTEM WITH INFANT MEASURING APPARATUS

(75) Inventor: Philip Michael Kenney, Baltimore, MD (US)

(73) Assignee: Hopkins Uniform Company, Baltimore, MD (US)

( * ) Notice: Subject to any disclaimer, the term of this patent is extended or adjusted under 35 U.S.C. 154(b) by 252 days.

(21) Appl. No.: 12/733,948

(22) PCT Filed: Oct. 6, 2008

(86) PCT No.: PCT/US2008/011504
§ 371 (c)(1),
(2), (4) Date: Mar. 31, 2010

(87) PCT Pub. No.: WO2009/045534
PCT Pub. Date: Apr. 9, 2009

(65) Prior Publication Data
US 2010/0229412 A1 Sep. 16, 2010

Related U.S. Application Data

(60) Provisional application No. 60/997,925, filed on Oct. 5, 2007.

(51) Int. Cl.
*A61B 5/107* (2006.01)
*G01B 1/00* (2006.01)
(52) U.S. Cl. ............................................. 33/512; 33/511
(58) Field of Classification Search .................... 33/511, 33/512, 515
See application file for complete search history.

(56) References Cited

U.S. PATENT DOCUMENTS

| | | | | |
|---|---|---|---|---|
| 5,499,457 A | * | 3/1996 | Weiler et al. | 33/512 |
| 5,884,408 A | * | 3/1999 | Simmons | 33/494 |
| 6,237,239 B1 | * | 5/2001 | Miyazaki | 33/512 |
| 6,256,896 B1 | * | 7/2001 | Landauer | 33/512 |
| 7,076,881 B1 | * | 7/2006 | Perry | 33/494 |
| 7,251,898 B2 | * | 8/2007 | Schafer et al. | 33/1 B |
| 7,340,842 B2 | * | 3/2008 | Rabe | 33/512 |
| 7,415,772 B1 | * | 8/2008 | Ferretti | 33/494 |
| 7,475,487 B1 | * | 1/2009 | Johnson | 33/512 |
| 7,665,220 B1 | * | 2/2010 | Gee | 33/511 |
| 7,683,272 B2 | * | 3/2010 | Hong | 177/126 |
| 7,893,367 B2 | * | 2/2011 | Gerster | 177/126 |
| 7,913,410 B2 | * | 3/2011 | Monturo | 33/506 |
| 8,006,400 B2 | * | 8/2011 | Gerster | 33/512 |

(Continued)

FOREIGN PATENT DOCUMENTS

WO WO 2009045534 A1 * 4/2009

*Primary Examiner* — Yaritza Guadalupe-McCall
(74) *Attorney, Agent, or Firm* — Marvin S. Townsend

(57) ABSTRACT

This Invention provides for a color-coded infant measuring apparatus (10) that includes a linear head panel (14), an antimicrobial flexible mat (12) having its top end connected to the linear head panel (14), and a linear foot panel (16) connected to the bottom end of the flexible mat (12). The flexible mat (12) includes a system of linear measurement comprising a plurality of line segments of different lengths representing integer measurement increments and fractional measurement increments, wherein line segments having the same length are assigned the same respective color. A plurality of different nonlinear two-dimensional symbols represents different fraction measurement increments, wherein the same two-dimensional symbols are assigned the same respective color and different two-dimensional symbols are assigned different colors. The flexible mat (12) includes a linear measuring scale on the central vertical line (37).

27 Claims, 8 Drawing Sheets

U.S. PATENT DOCUMENTS

| | | | |
|---|---|---|---|
| 8,021,158 B2 * | 9/2011 | Eras et al. | 33/454 |
| 2005/0204471 A1 * | 9/2005 | Ruiz | 5/420 |
| 2005/0278967 A1 * | 12/2005 | Du Plessis | 33/493 |
| 2006/0005460 A1 * | 1/2006 | Bittrick | 43/43.4 |
| 2007/0240326 A1 * | 10/2007 | Cerbelli et al. | 33/755 |
| 2008/0034600 A1 * | 2/2008 | Rabe | 33/512 |
| 2008/0261184 A1 * | 10/2008 | Eras et al. | 33/494 |
| 2010/0088915 A1 * | 4/2010 | Neff | 33/759 |
| 2010/0229412 A1 * | 9/2010 | Kenney | 33/512 |

* cited by examiner

RECOMMENDED PROCEDURES
1) HOLD CHILD FLAT ON FLEXIBLE MAT 12
2) FEET FLAT AGAINST LINEAR FOOT PANEL 16
3) HANDS ON KNEES
4) LEGS STRAIGHT
5) ARMS COMFORTABLY STRAIGHT
6) HANDS CUPPED UNDER JAW/OVER EARS
7) HEAD AGAINST THE LINEAR HEAD PANEL 14

LINE OF SIGHT PERPENDICULAR TO FLEXIBLE MAT 12

GENERAL MEASURING SYSTEM WITH INFANT MEASURING APPARATUS

CROSS-REFERENCE TO RELATED APPLICATION

This application claims priority based upon copending U.S. Provisional Application of Kenney, Ser. No. 60/997,925, Filing Date 5 Oct. 2007, for "Infant Measuring System".

TECHNICAL FIELD

The present invention relates generally to methods and apparatus for measuring the length of infants. More particularly, the present invention provides an flexible mat that has systems of measuring scales thereon.

BACKGROUND ART

With respect to an infant measuring apparatus, a number of infant measuring apparatuses are well known in the art.

More specifically, throughout the years, a number of innovations have been developed relating to infant measuring apparatuses, and the following U.S. patents and published U.S. patent application are representative of some of those innovations:

| | |
|---|---|
| 2,197,031 | Davis |
| 3,020,643 | Moran |
| 4,939,849 | Johnson |
| 7,340,842 | Rabe |
| 2005/0204471 | Ruiz |

Davis (U.S. Pat. No. 2,197,031) discloses a flexible child's measuring record which includes a pair of rollers located at opposite ends of a flexible rollable measuring member which has a measuring scale thereon.

Moran (U.S. Pat. No. 3,020,643) discloses a flexible device for measuring an infant's height. The device has a linear foot panel. The flexible measuring device is rolled onto a roller which is retained in a box-like housing. The box-like housing has a mounting bracket for mounting the housing onto a table top.

Johnson (U.S. Pat. No. 4,939,849) discloses an infant measuring device that has a linear head panel and a linear foot panel. The linear head panel is fixed, and the linear foot panel is movable with respect to the linear head panel. Measuring scales are located along the sides of the area onto which the infant is placed. The area onto which the infant is placed is rigid, not flexible.

Rabe (U.S. Pat. No. 7,340,842) discloses an infant measuring article in the form a flexible bedding article, such as a blanket. A measuring scale is centrally located within the measuring article.

Ruiz (2005/0204471) discloses a baby measuring mat which has a top layer, a bottom layer, and a middle layer. The middle layer is comprised of an open cell foam material that cushions the mat.

In addition to the patents and published patent application cited above, also in the prior art are the following commercially available products:

Seca Model No. 210 from Seca Corporation, 8920 A Route 108, Columbia, Md. 21045, USA; and Starter's Measure Mat is from Slater & Frith LTD. More specifically, Starter's Measure Mat is from Slater & Frith LTD, Lurista House, Stalham Road, Wroxham, Norwich NR128DV, United Kingdom.

More specifically, the Seca Model No. 210 is an infant measuring mat that has a central longitudinal line, a pair of inch-based measuring scales that straddle the central longitudinal line, and a pair of metric-based measuring scales that straddle the pair of inch-based scales. Neither the inch-based scales nor the metric-based scales employ color-coding. All scale increments are entirely one color—black. Seca Model No. 210 has a linear head panel, a top end of a flexible mat connected to the linear head panel, and a linear foot panel connected to a bottom end of the flexible mat. The scales of the Seca Model No. 210 are located on the flexible mat. An infant is placed on the flexible mat between the linear head panel and the linear foot panel, and the length of the infant is measured by looking at the measuring scales on the flexible mat.

With Seca Model No. 210, one-size circles are the only nonlinear two-dimensional-symbol-coding elements employed for the inch measuring scales, and the one-size circles represent half-inch increments. There is no measuring scale on the central longitudinal line. Also, there are no increment marks for ⅛, ⅜, ⅝, and ⅞ inches. Therefore, the Seca Model No. 210 does not permit accurate measurements of ⅛, ⅜, ⅝, and ⅞ inches. Also, for the inch measuring scales, the only linear-coding scheme includes counterintuitive shorter shared line segments for integral inch marks and longer shared line segments for one-half inch marks.

Also, with Seca Model No. 210, a pair of metric scales straddle the pair of inch scales. Relatively long horizontal lines are used for integral centimeter increments, and relatively short horizontal lines are used for one-half centimeter increments. In addition, one-size circles are also used for one-half centimeter increments. The one-size circles lie on respective longitudinal lines. The presence of the black one-size circles on the black longitudinal lines makes it difficult to read the one-size circles on the longitudinal lines. In addition, the use of black one-size circles for both one-half inch increments and one-half centimeter increments can lead to confusion. Also, for the metric scales, only integral centimeter increment and half-centimeter increment scale marks are provided. There are no fractional centimeter increment scale marks for 0.1, 0.2, 0.3, 0.4, 0.6, 0.7, 0.8, and 0.9 centimeter increments.

Turning to the Starter's Measure Mat, an infant measuring mat is provided in which a pair of inch-based measuring scales straddle a center portion, and a pair of metric-based measuring scales straddle pair of inch-based measuring scales. Both the inch-based and the metric-based measuring scales employ two colors, white and black.

With Starter's Measure Mat, both of the inch-based measuring scales are located equidistant from and straddle the center portion, but there is no central longitudinal line at the center portion. Each of the pair of the inch measuring scales has a longitudinal line associated with the respective scale. Black is used for one inch increment lines and for one-half inch increment lines. White is used for quarter-inch increment one-size circles. There is no central inch-based measuring scale. Also, there are no increment marks for ⅛, ⅜, ⅝, and ⅞ inches. Also, counterintuitively, same length shared lines are used for both integral inch increments and half-inch increments.

With Starter's Measure Mat, each of the pair of metric measuring scales includes a respective longitudinal line, short black lines for integral centimeter increments, and white one-size circles for half-centimeter increments. Clearly, the use of one-size white circles for both one-half inch increments and one-half centimeters can lead to confusion.

With respect to a general measuring system, a number of measuring systems are well known in the art. More specifically, throughout the years, a number of innovations have been developed relating to measuring systems, and the following U.S. patents are representative of some of those innovations:

| | |
|---|---|
| 861,799 | Briel |
| 5,012,590 | Wagner et al |
| 5,335,421 | Jones |
| 5,487,223 | Krane |
| 5,497,558 | Wagner |
| 5,501,019 | Concari et al |
| 5,884,408 | Simmons |

Briel (U.S. Pat. No. 861,799) discloses a measuring rule that has increment markings which appear to be two-dimensional symbols that look like nails. All increments and fractional increments have the same two-dimensional nail symbol. Smaller fractions employ smaller two-dimensional nail symbols. There is no color coding. There is no second two-dimensional symbol.

Wagner et al (U.S. Pat. No. 5,012,590) disclose a disposable layout tape that uses a number of two-dimensional symbols which include simulated human feet, circles, triangles, and squares at various increments. There are no half-increments, quarter-increments, or eighth-increments. There is a disclosure of diamond symbols 30 divided into two contiguous half-diamonds 30a and 30b. Circle symbols 28 are divided into two contiguous half-circles 28a and 28b. All half-symbol portions 28a and 30a would be of a first color and all of half-symbol portions 28b and 30b would be of a second color, which contrasts with the first color, and for this purpose white and black are considered to be colors.

Jones (U.S. Pat. No. 5,335,421) discloses rules which have blue line segments for eighth of an inch increments and which have shorter red line segments for sixteenth of an inch increments. The inch, half-inch, and quarter-inch line segments are all the same color. There is no first two-dimensional symbol for representing fractional-increments.

Krane (U.S. Pat. No. 5,487,223) discloses a linear scale that has a first two-dimensional diamond symbol for integers and a second two-dimensional pencil-like symbol for all fractions. There is no color coding. There is only one two-dimensional symbol for all fractional-increments. That is, there is no two-dimensional symbol that differentiates between quarter-increments and eighth-increments.

Wagner (U.S. Pat. No. 5,497,558) discloses a multi-functional drafting instrument which includes large two-dimensional hexagons for integers and small two-dimensional hexagons for fractions. There is no color coding. There is no second two-dimensional symbol. There are no quarter-increments and no eighth increments.

Concari et al (U.S. Pat. No. 5,501,019) disclose three types of partially filled circles. Quarter-filled circles represent quarter inches. Half-filled circles represent half inches. Three-quarter-filled circles represent three-quarter inches. There is no color coding. There are no single first two-dimensional symbol which represents all quarter-increments and three-quarter increments. There is no single second two-dimensional symbol which represents all of eighth-increments, three-eighth-increments, five-eighth-increments, and seven-eighth-increments.

Simmons (U.S. Pat. No. 5,884,408) discloses a graduated measuring device with color coded indicia. All integral increments and fractional increments use line segments of different lengths. There are no two-dimensional symbols for representing increments. There are just short line segments. There are eight separate color codes for respective integral-increments, eighth-increments, quarter-increments, three-eighth-increments, half-increments, five-eighth-increments, three-quarter-increments, and seven-eighth-increments. There are no two-dimensional symbols for representing increments. There is no single third coding color which represents quarter-increments and three-quarter increments. There is no single fourth coding color which represents eighth-increments, three-eighth-increments, five-eighth-increments, and seven-eighth-increments.

Having reviewed the prior art above, in relation to both infant measuring apparatuses and general measuring systems, the following features that would be desirable are not disclosed in the prior art.

None of the prior art discloses an infant measuring apparatus that has a central vertical line that has a measuring scale on the central vertical line. However, it would be desirable for an infant measuring apparatus to have a central vertical line on a flexible mat that has a measuring scale on the central vertical line.

None of the prior art discloses an infant measuring apparatus having a flexible mat having a measuring system which employs a plurality of line segments of different lengths representing integer measurement increments and fractional measurement increments, where all line segments having the same length are assigned the same respective color in a color coding scheme. However, it would be desirable if such a measuring system were employed, especially on an flexible mat.

None of the prior art discloses an infant measuring apparatus having a flexible mat having a measuring system which employs a plurality of different nonlinear two-dimensional symbols representing different fractional measurement increments, wherein all of the same two-dimensional symbols are assigned the same respective color in the color coding scheme, and wherein different two-dimensional symbols are assigned different colors in the color coding scheme. However, it would be desirable if such a measuring system were employed, especially on an flexible mat.

None of the prior art discloses an infant measuring apparatus having a flexible mat having a measuring system which employs line segments of different lengths which are color coded and different nonlinear two-dimensional symbols which are color coded such that line segments and nonlinear two-dimensional symbols which represent the same fractional measurement increments have the same coded color. However, it would be desirable if such a measuring system were employed, especially on an flexible mat.

None of the prior art discloses an infant measuring apparatus having a flexible mat having an inch-based measuring system which employs first nonlinear two-dimensional symbols representing quarter-increments and three-quarter increments which are color coded with one coding color, and second nonlinear two-dimensional symbols representing eighth-increments, three-eighth-increments, five-eighth-increments, and seven-eighth-increments which are color coded with another coding color, wherein the first two-dimensional symbols and the second two-dimensional symbols are not the same two-dimensional symbols. However, it would be desirable if such a measuring system were employed, especially on an flexible mat.

None of the prior art discloses an infant measuring apparatus having a flexible mat having a metric-based measuring system which employs first line segments representing integral-increments which are color coded with a first coding color, which employs second line segments representing half-increments which are color coded with a second coding color, and employs third line segments representing nonhalf-fractional-increments which are color coded with a third coding color. However, it would be desirable if such a measuring system were employed, especially on an flexible mat.

None of the prior art discloses an infant measuring apparatus having a flexible mat having a measuring system which employs a measuring system that can be very helpful to dyslectic individuals for improving and facilitating measuring accuracy and consistency and can facilitate quicker learning and greater retention. However, it would be desirable if such a measuring system were employed, especially on an flexible mat.

None of the prior art discloses general measuring systems, described herein as desirable in connection with infant measuring apparatuses, which can also be used independently of infant measuring apparatuses in a wide variety of applications such as with tape measures, disposable tapes, rulers, etc. However, it would be desirable if such general measuring systems were provided.

None of the prior art discussed above discloses either infant measuring apparatuses or general measuring systems which can be especially useful for blind persons, whereby three-dimensional lines segments and three-dimensional symbols are provided.

None of the prior art discloses an infant measuring apparatus having a flexible mat having a measuring system which employs a metric-based measuring system that employs first line segments representing integral-increments, wherein the first line segments have a first line length, a first line thickness, and are color coded with a first coding color, which employs second line segments representing half-increments, wherein the second line segments have a second line length, a second line thickness, and are color coded with a second coding color, and employs third line segments representing nonhalf-fractional-increments, wherein the third line segments have a third line length, a third line thickness, and are color coded with a third coding color. However, it would be desirable if such a measuring system were employed, especially on an flexible mat.

Thus, while the foregoing body of prior art indicates it to be well known to use infant measuring apparatuses having measuring systems, the prior art described above does not teach or suggest a general measuring system or an infant measuring apparatus which has the following combination of desirable features: (1) provides a central vertical line on a flexible mat that has a measuring scale on the central vertical line; (2) has a measuring system which employs a plurality of line segments of different lengths representing integer measurement increments and fractional measurement increments, where all line segments having the same length are assigned the same respective color in a color coding scheme; (3) has a measuring system which employs a plurality of different nonlinear two-dimensional symbols representing different fractional measurement increments, wherein all of the same two-dimensional symbols are assigned the same respective color in the color coding scheme, and wherein different two-dimensional symbols are assigned different colors in the color coding scheme; (4) has a measuring system which employs line segments of different lengths which are color coded and different nonlinear two-dimensional symbols which are color coded such that the line segments and the nonlinear two-dimensional symbols which represent the same fractional measurement increments have the same coded color; (5) has an inch-based measuring system which employs first nonlinear two-dimensional symbols representing quarter-increments and three-quarter increments which are color coded with one coding color, and second nonlinear two-dimensional symbols representing eighth-increments, three-eighth-increments, five-eighth-increments, and seven-eighth-increments which are color coded with another coding color, wherein the first two-dimensional symbols and the second two-dimensional symbols are not the same two-dimensional symbols; (6) provides a metric-based measuring system that employs first line segments representing integral-increments, wherein the first line segments have a first line length, a first line thickness, and are color coded with a first coding color, which also employs second line segments representing half-increments, wherein the second line segments have a second line length, a second line thickness, and are color coded with a second coding color, and which also employs third line segments representing nonhalf-fractional-increments, wherein the third line segments have a third line length, a third line thickness, and are color coded with a third coding color; (7) has a measuring system that can be very helpful to dyslectic individuals for improving and facilitating measuring accuracy and consistency and can facilitate quicker learning and greater retention; (8) provides general measuring systems, described herein as desirable in connection with infant measuring apparatuses, which can also be used independently of infant measuring apparatuses in a wide variety of applications such as with tape measures, disposable tapes, rulers, etc.; and (9) provides either infant measuring apparatuses or general measuring systems which can be especially useful for blind persons, whereby three-dimensional lines segments and three-dimensional symbols are employed.

The foregoing desired characteristics are provided by the unique general measuring system and infant measuring apparatus of the present invention as will be made apparent from the following description thereof. Other advantages of the present invention over the prior art also will be rendered evident.

DISCLOSURE OF INVENTION

To achieve the foregoing and other advantages, the present invention, provides an apparatus which includes an inch-based measurement scale only, but could also be adapted to a metric-only measurement scale. Such an infant measuring apparatus includes a linear head panel. A flexible mat has at top end is connected to the linear head panel, and a linear foot panel is connected to a bottom end of the flexible mat. The flexible mat includes thereon a system of linear measurement which includes a first linear scale which is comprised of a plurality of line segments of different lengths representing integer measurement increments and fractional measurement increments, where all line segments having the same length are assigned the same respective color in a color coding scheme. A plurality of different nonlinear two-dimensional symbols represent different fractional measurement increments, wherein all of the same two-dimensional symbols are assigned the same respective color in the color coding scheme, and wherein different two-dimensional symbols are assigned different colors in the color coding scheme.

Preferably, the linear head panel is connected to a head panel base. The linear head panel is perpendicular to the head panel base, and the linear foot panel is connected to a foot panel base. The linear foot panel is perpendicular to the foot panel base.

The line segments of different lengths and the different nonlinear two-dimensional symbols are color coded such that line segments and nonlinear two-dimensional symbols which represent the same fractional measurement increment have the same coded color.

With one embodiment, the line segments include first line segments representing integral-increments. The first line segments have a first line length, a first line thickness, and are color coded with a first coding color. Second line segments represent half-increments. The second line segments have a second line length, a second line thickness, and are color coded with a second coding color.

The nonlinear two-dimensional symbols include first nonlinear two-dimensional symbols representing quarter-increments and three-quarter increments which are color coded with a third coding color. Second nonlinear two-dimensional symbols represent eighth-increments, three-eighth-increments, five-eighth-increments, and seven-eighth-increments which are color coded with a fourth coding color. The first two-dimensional symbols and the second two-dimensional symbols are not the same two-dimensional symbols.

For an apparatus which includes an inch-based measurement scale in conjunction with a metric measurement scale, the inch-only inch-based measurement scale described above further includes the following features of a metric measurement scale. However, as noted above, the principles of the inch-only based measurement scale can also be adapted to a metric measurement scale if desired. For the added metric scale, the system of linear measurement further includes third line segments representing integral-centimeter increments. The third line segments have a third line length, a third line thickness, and are color coded with a fifth coding color. Fourth line segments represent half-centimeter increments. The fourth line segments have a fourth line length, a fourth line thickness, and are color coded with a sixth coding color. Fifth line segments represent nonhalf-centimeter fractional-increments. The fifth line segments have a fifth line length, a fifth line thickness, and are color coded with a seventh coding color.

The fifth color coding and the first color coding can be the same color. The fifth color coding and the first color coding can be blue.

The seventh color coding and the second color coding can be the same color. The seventh color coding and the second color coding can be black.

For a metric measurement scale alone, without the presence of an inch-based measurement scale (and not adapted from the inch-only measurement scale described above), the subject invention provides infant measuring apparatus which includes a linear head panel, a flexible mat having a top end which is connected to the linear head panel. A linear foot panel is connected to a bottom end of the flexible mat. The flexible mat includes thereon a system of linear measurement which includes a linear scale that is comprised of first line segments representing integral-increments. The first line segments have a first line length, a first line thickness, and are color coded with a first coding color. Second line segments represent half-increments. The second line segments have a second line length, a second line thickness, and are color coded with a second coding color. Third line segments represent nonhalf-fractional-increments. The third line segments have a third line length, a third line thickness, and are color coded with a third coding color.

The first coding color can be blue. The second coding color can be gray, and the third coding color can be black.

Now, the discussion turns from infant measuring apparatuses to systems of linear measurement, in accordance with the invention.

For a system of linear measurement which includes an inch-based measurement scale only, but could also be adapted to a metric-only measurement scale, a system of linear measurement includes a first linear scale that is comprised of a plurality of line segments of different lengths representing integer measurement increments and fractional measurement increments, where all line segments having the same length are assigned the same respective color in a color coding scheme. A plurality of different nonlinear two-dimensional symbols represent different fractional measurement increments. All of the same two-dimensional symbols are assigned the same respective color in the color coding scheme. Different two-dimensional symbols are assigned different colors in the color coding scheme.

Preferably, the line segments of different lengths and the different nonlinear two-dimensional symbols are color coded such that line segments and nonlinear two-dimensional symbols which represent the same fractional measurement increment have the same coded color.

The line segments can include first line segments which represent integral-increments. The first line segments have a first line length, a first line thickness, and are color coded with a first coding color. Second line segments represent half-increments. The second line segments have a second line length, a second line thickness, and are color coded with a second coding color.

The nonlinear two-dimensional symbols include first nonlinear two-dimensional symbols representing quarter-increments and three-quarter increments which are color coded with a third coding color. Second nonlinear two-dimensional symbols represent eighth-increments, three-eighth-increments, five-eighth-increments, and seven-eighth-increments which are color coded with a fourth coding color.

The first two-dimensional symbols and the second two-dimensional symbols are not the same two-dimensional symbols.

For a system of linear measurement which includes an inch-based measurement scale in conjunction with a metric measurement scale, the inch-only inch-based measurement scale described above further includes the following features of a metric measurement scale. However, as noted above, the principles of the inch-only based measurement scale can also be adapted to a metric measurement scale if desired.

The added metric measurement scale is comprised of third line segments representing integral-metric increments. The third line segments have a third line length, a third line thickness, and are color coded with a fifth coding color. Fourth line segments represent half-metric increments. The fourth line segments have a fourth line length, a fourth line thickness, and are color coded with a sixth coding color. Fifth line segments represent nonhalf-fractional-metric increments. The fifth line segments have a fifth line length, a fifth line thickness, and are color coded with a seventh coding color.

The fifth color coding and the first color coding can be the same color. The fifth color coding and the first color coding can be blue.

The seventh color coding and the second color coding can be the same color. The seventh color coding and the second color coding can be black.

For a metric measurement scale alone, without the presence of an inch-based measurement scale (and not adapted from the inch-only measurement scale described above), the subject invention provides a system of metric linear measurement which includes a linear scale which is comprised of first line segments representing integral-metric increments. The first line segments have a first line length, a first line thickness, and are color coded with a first coding color. Second line segments represent half-metric increments. The second line segments have a second line length, a second line thickness, and are color coded with a second coding color. Third line segments represent nonhalf-fractional-metric increments. The third line segments have a third line length, a third line thickness, and are color coded with a third coding color.

The first coding color can be blue, the second coding color can be gray, and the third coding color can be black.

In addition to the two-dimensional embodiments discussed above, the present invention provides three-dimensional embodiments.

In this respect, a system of linear measurement includes a three-dimensional linear scale which is comprised of a plurality of three-dimensional line segments of different lengths representing integer measurement increments and fractional measurement increments. A plurality of different nonlinear three-dimensional symbols represent different fractional measurement increments and different three-dimensional numerical integer symbols.

The three-dimensional line segments can include first three-dimensional line segments representing integral-increments. The first line segments have a first line length and a first line thickness. Second three-dimensional line segments represent half-increments. The second line segments have a second line length and a second line thickness.

The nonlinear three-dimensional symbols can include first nonlinear three-dimensional symbols representing quarter-increments and three-quarter increments. Second nonlinear three-dimensional symbols represent eighth-increments, three-eighth-increments, five-eighth-increments, and seven-eighth-increments. The first three-dimensional symbols and the second three-dimensional symbols are not the same three-dimensional symbols.

If desired the three-dimensional line segments and the three-dimensional symbols can be color coded in the same manner as the two-dimensional line segments and the two-dimensional symbols described above. The three-dimensional numerical integer symbols can be any desirable color.

In view of the above, an object of the present invention is to provide a new and improved general measuring system and infant measuring apparatus which provides a central vertical line on a flexible mat that has a measuring scale on the central vertical line.

Still another object of the present invention is to provide a new and improved general measuring system and infant measuring apparatus that has a measuring system which employs a plurality of line segments of different lengths representing integer measurement increments and fractional measurement increments, where all line segments having the same length are assigned the same respective color in a color coding scheme.

Yet another object of the present invention is to provide a new and improved general measuring system and infant measuring apparatus which has a measuring system which employs a plurality of different nonlinear two-dimensional symbols representing different fractional measurement increments, wherein all of the same two-dimensional symbols are assigned the same respective color in the color coding scheme, and wherein different two-dimensional symbols are assigned different colors in the color coding scheme.

Even another object of the present invention is to provide a new and improved general measuring system and infant measuring apparatus that has a measuring system which employs line segments of different lengths which are color coded and different nonlinear two-dimensional symbols which are color coded such that the line segments and the nonlinear two-dimensional symbols which represent the same fractional measurement increments have the same coded color.

Still a further object of the present invention is to provide a new and improved general measuring system and infant measuring apparatus which has an inch-based measuring system which employs first nonlinear two-dimensional symbols representing quarter-increments and three-quarter increments which are color coded with one coding color, and second nonlinear two-dimensional symbols representing eighth-increments, three-eighth-increments, five-eighth-increments, and seven-eighth-increments which are color coded with another coding color, wherein the first two-dimensional symbols and the second two-dimensional symbols are not the same two-dimensional symbols.

Yet another object of the present invention is to provide a new and improved general measuring system and infant measuring apparatus that provides a metric-based measuring system that employs first line segments representing integral-increments, wherein the first line segments have a first line length, a first line thickness, and are color coded with a first coding color, which also employs second line segments representing half-increments, wherein the second line segments have a second line length, a second line thickness, and are color coded with a second coding color, and which also employs third line segments representing nonhalf-fractional-increments, wherein the third line segments have a third line length, a third line thickness, and are color coded with a third coding color.

Still another object of the present invention is to provide a new and improved general measuring system and infant measuring apparatus which has a measuring system that can be very helpful to dyslectic individuals for improving and facilitating measuring accuracy and consistency and can facilitate quicker learning and greater retention.

Yet another object of the present invention is to provide a new and improved general measuring system and infant measuring apparatus that provides general measuring systems, described herein as desirable in connection with infant measuring apparatuses, which can also be used independently of infant measuring apparatuses in a wide variety of applications such as with tape measures, disposable tapes, rulers, etc.

Still a further object of the present invention is to provide a new and improved general measuring system and infant measuring apparatus that provides either infant measuring apparatuses or general measuring systems which can be especially useful for blind persons, whereby three-dimensional lines segments and three-dimensional symbols are employed.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawings wherein.

MODES FOR CARRYING OUT THE INVENTION

Figure 1:
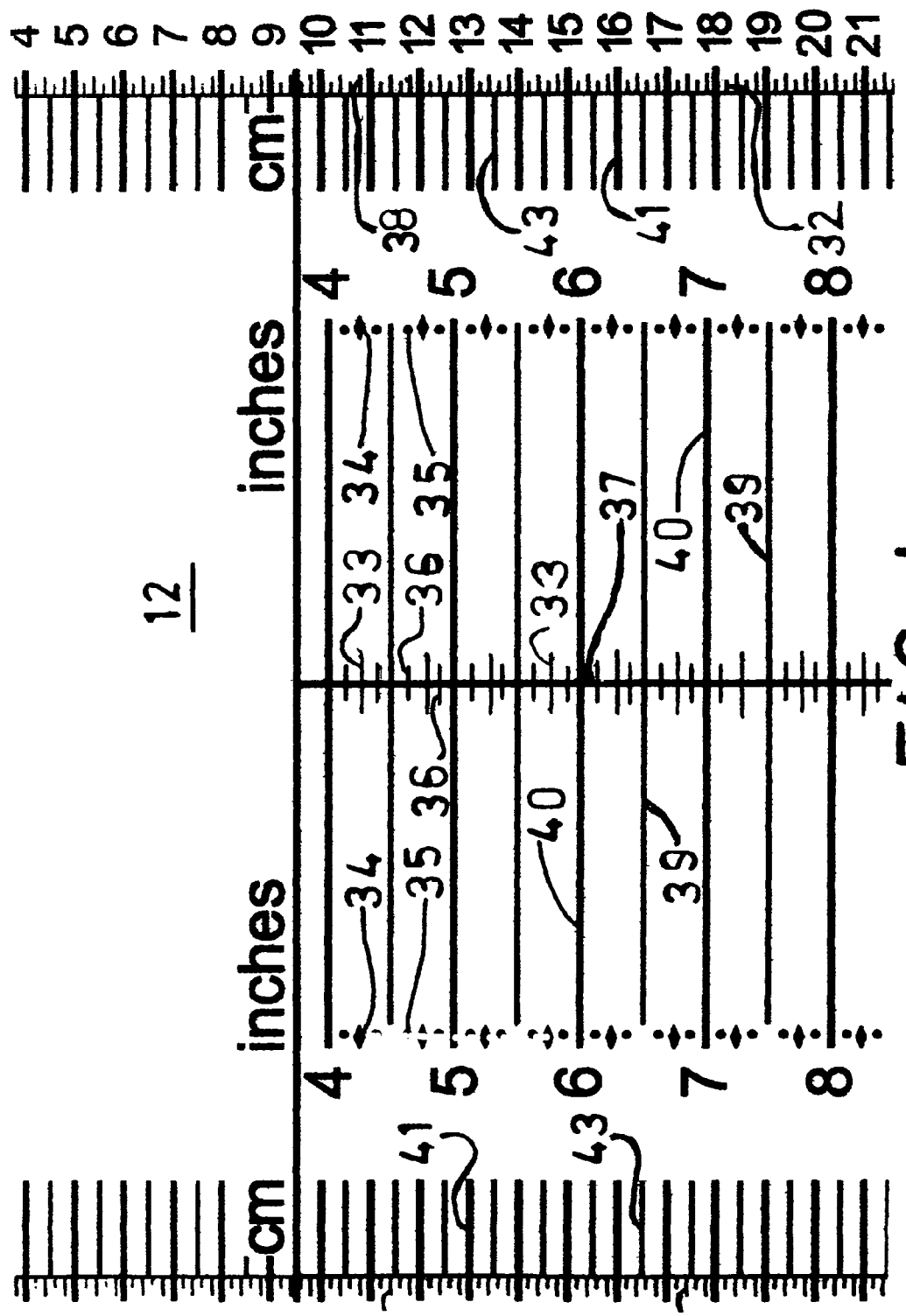
FIG. 1 is a top view of a portion of a general measuring system used in a measuring scale on a flexible mat in a preferred embodiment of an infant measuring apparatus of the invention.

Turning to FIGS. 1-4, there is shown a first embodiment of the infant measuring apparatus of the invention generally designated by reference numeral 10. The infant measuring apparatus 10 includes a general measurement system. In each of the figures, reference numerals are shown that correspond to like reference numerals that designate like elements shown in other figures.

FIG. 1 is a top view of a portion of a general measuring system used in a measuring scale on a flexible mat 12 in a preferred embodiment of an infant measuring apparatus 10 of the invention.

It is noted that the measurement system shown in FIG. 1 can be used on a wide variety of surfaces, especially flat surfaces.

Figure 4:
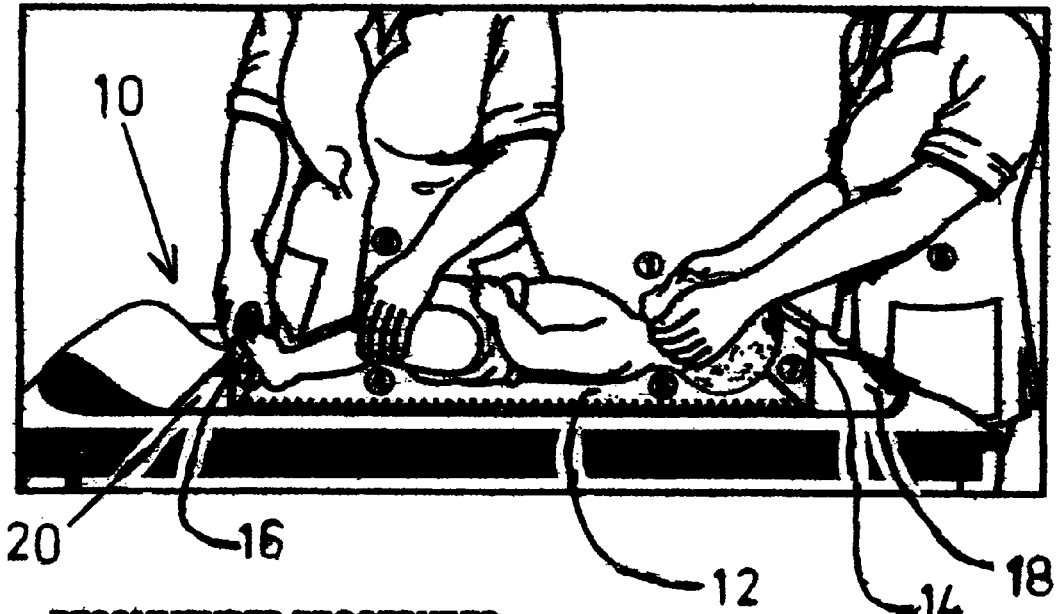
FIG. 4 shows a perspective view of an embodiment of infant measuring apparatus which includes an infant lying upon on the flexible mat, a portion of which is shown in FIG. 1, between the linear head panel and the linear foot panel, and wherein the infant is being cared for by health care personnel.
Figure 4:

The overall infant measuring apparatus 10 is shown in FIG. 4 to include the flexible mat 12 located between a linear head panel 14 and a linear foot panel 16.

Figure 2:
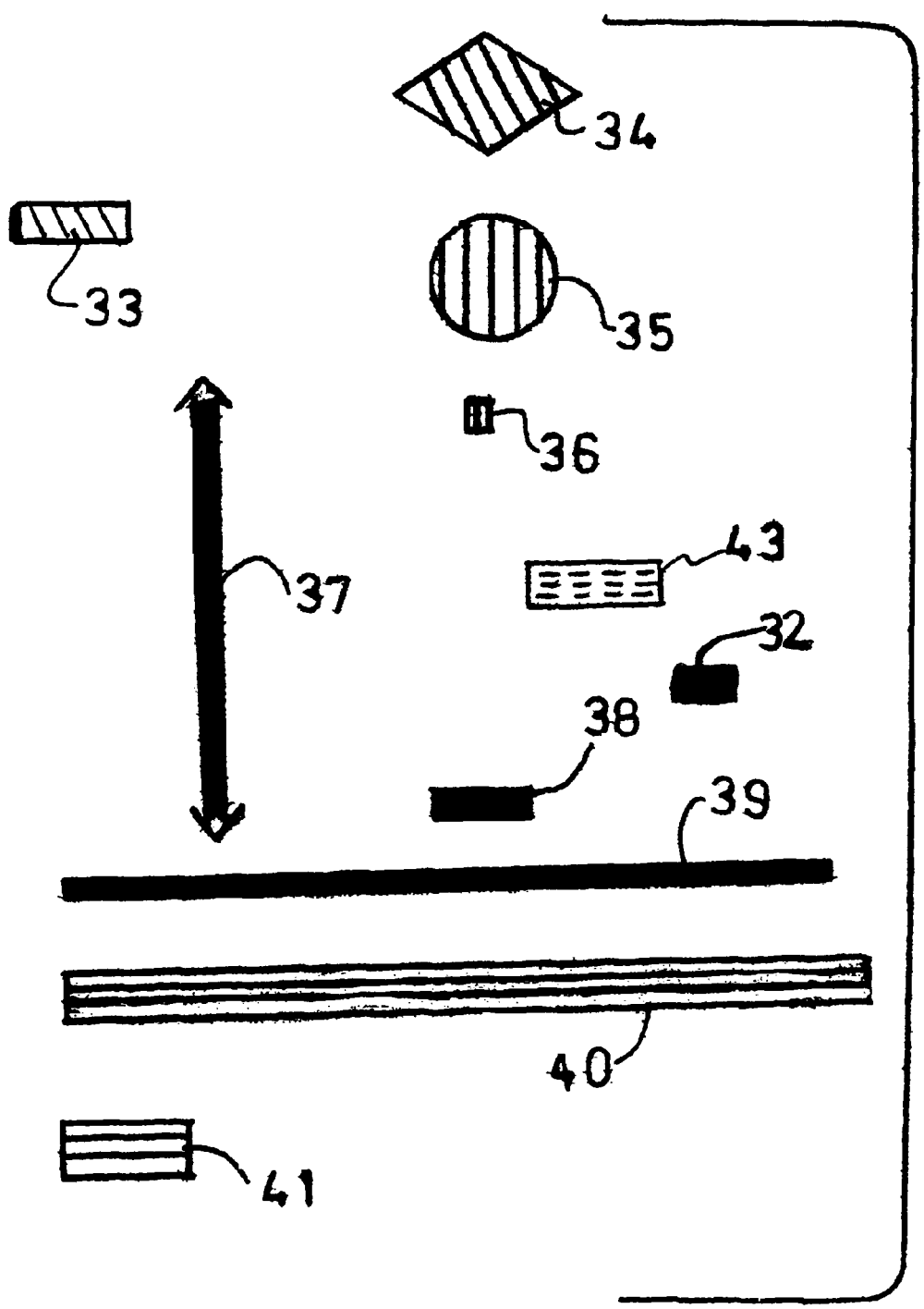
FIG. 2 is a collection of color coded lines and color coded two-dimensional symbols used in the general measuring system and on the flexible mat shown in FIG. 1.

FIG. 2 is a collection of color coded lines and color coded two-dimensional symbols used in the general measuring system and on the flexible mat shown in FIG. 1.

Figure 3:
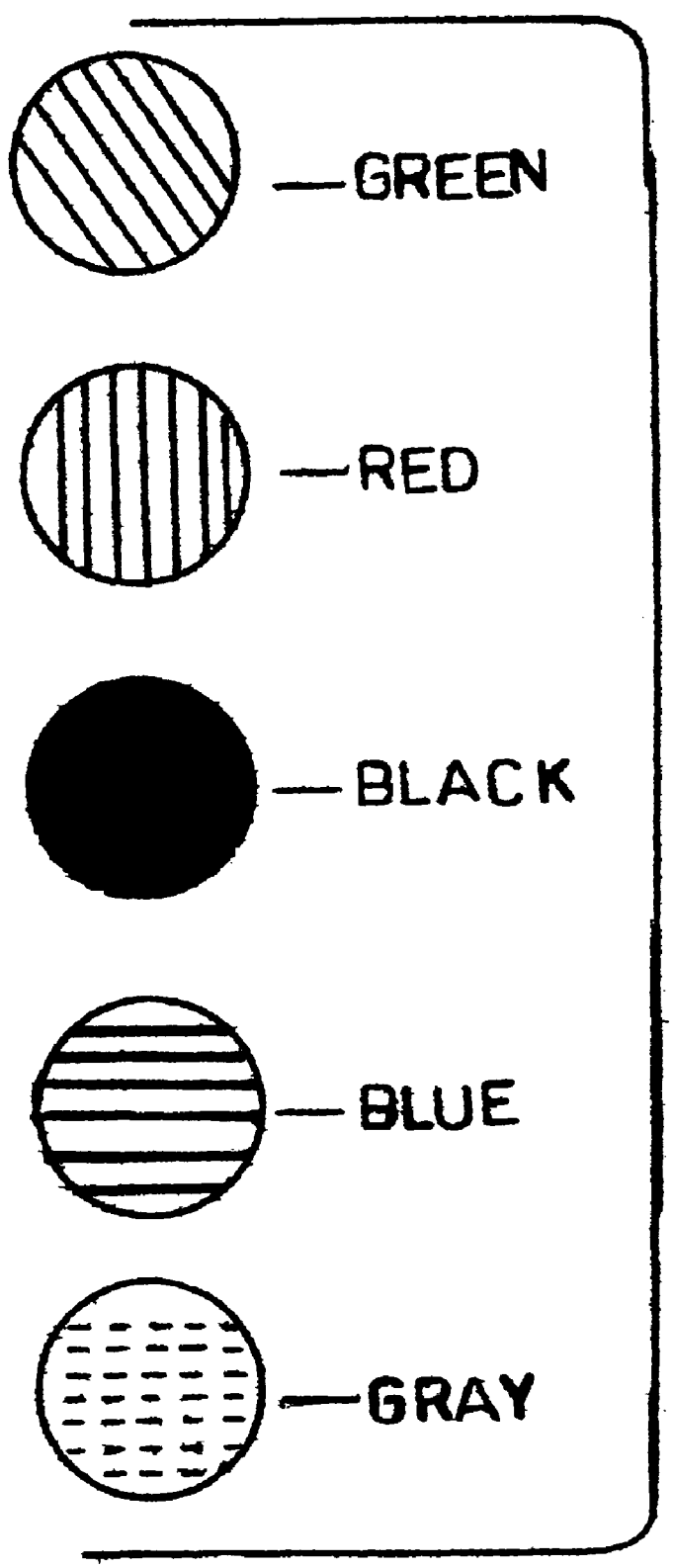
FIG. 3 is an array of specific colors in a color coding scheme which is used in the lines and two-dimensional symbols shown in FIG. 2.

FIG. 3 is an array of specific colors in a color coding scheme which is used for the lines and two-dimensional symbols shown in FIG. 2 on the flexible mat 12 shown in FIG. 1 and FIG. 4.

FIG. 4 shows a perspective view of an embodiment of infant measuring apparatus which includes an infant lying upon on the flexible mat 12, a portion of which is shown in FIG. 1, between the linear head panel 14 and the linear foot panel 16, and wherein the infant is being cared for by health care personnel. More discussion with respect to FIG. 4 is presented below.

More specifically, FIG. 1 shows a pair of first inch measuring scales, a second inch measuring scale which is straddled by the pair of first inch measuring scales, and a pair of metric measuring scales that straddle the pair of first inch measuring scales.

More specifically, for the pair of first inch measuring scales on the flexible mat 12, the subject two-dimensional symbols can include two-dimensional green diamond symbols 34 representing one-quarter inch increments, two-dimensional red circle symbols 35 representing one-eighth inch increments, a central two-dimensional black vertical line symbol 37 placed as a longitudinal orientation line, two-dimensional longest blue horizontal line symbols 40 representing integer inch increments, and two-dimensional first-intermediate-length black horizontal line symbols 39 representing one-half inch increments. In addition, integral numbers representing integral inches are located next to the two-dimensional longest blue horizontal line symbols 40.

More specifically, for the second inch measuring scale on the flexible mat 12 and intersecting the two-dimensional black central vertical line symbol 37, the subject two-dimensional symbols can include the two-dimensional longest blue horizontal line symbols 40 which intersect the two-dimensional black central vertical line symbol 37 and which represent integer inch increments, can include the two-dimensional first-intermediate-length black horizontal line symbols 39 which intersect the two-dimensional black central vertical line symbol 37 and represent one-half inch increments, can include the two-dimensional green horizontal line symbols 33 which intersect the two-dimensional black central vertical line symbol 37 and represent one-quarter inch increments, and can include the two-dimensional red horizontal line symbols 36 which intersect the two-dimensional black central vertical line symbol 37 and represent one-eighth inch increments.

More specifically, for the pair of metric measuring scales that straddle the pair of first inch measuring scales, two-dimensional shorter blue horizontal line symbols 41 represent integer centimeter increments. Two-dimensional gray horizontal line symbols 43 represent 0.5 centimeter (5 millimeter) increments. Two-dimensional second-intermediate-length black horizontal line symbols 38 represent 0.2 centimeter (2 millimeter) increments. Two-dimensional shortest length black horizontal line symbols 32 represent 0.2 centimeter (2 millimeter) increments.

It is noted that, preferably, with the metric-based measurement system, the two-dimensional shortest length black horizontal line symbols 32 and the two-dimensional second-intermediate-length black horizontal line symbols 38, which each represent 0.2 centimeter increments, can be replaced by common length two-dimensional black horizontal line symbols (not referenced) that each represent 0.1 centimeter (1 millimeter).

FIG. 3 is an array of specific colors in a color coding scheme which is used in the lines and two-dimensional symbols shown in FIG. 2 and that are employed in FIG. 1.

The following two-dimensional symbols have been disclosed: diamonds and circles.

However, it is understood that a wide variety of two-dimensional symbols can be employed, such as squares, triangles, four-sided polygons, five-sided polygons, six-sided polygons, ovals, spheroids, and asterisks, among many others.

The following colors have been thus far disclosed in FIG. 3 for color coding: green, red, black, blue, and gray.

However, it is understood that a wide variety of colors can be used for color coding with the subject invention.

Aside from the colors specifically disclosed in FIG. 3, other suitable colors include white, pink, orange, brown, yellow, cyan, and violet.

In addition, here is a more comprehensive list of other colors that can be used for color coding with the subject invention: Alice blue, Alizarin, Amaranth, Amber, Amethyst, Apricot, Aqua, Aquamarine, Army green, Asparagus, Atomic tangerine, Auburn, Azure (color wheel), Azure (web), Baby blue, Beige, Bistre, Black, Blue, Blue (pigment), Blue (RYB), Blue-green, Blue-violet, Bondi blue, Brass, Bright green, Bright pink, Bright turquoise, Brilliant rose, Bronze, Brown, Buff, Burgundy, Burnt orange, Burnt sienna, Burnt umber, Camouflage green, Caput Mortuum, Cardinal, Carmine, Carnation pink, Carolina blue, Carrot orange, Celadon, Cerise, Cerulean, Cerulean blue, Chartreuse (traditional), Chartreuse (web), Cherry blossom pink, Chestnut, Chocolate, Cinnabar, Cinnamon, Cobalt, Columbia blue, Copper, Copper rose, Coral, Coral red, Corn, Cornflower blue, Cosmic latte, Cream, Crimson, Cyan, Cyan (process), Dark blue, Dark brown, Dark cerulean, Dark chestnut, Dark coral, Dark goldenrod, Dark green, Dark khaki, Dark pastel green, Dark pink, Dark scarlet, Dark salmon, Dark slate gray, Dark spring green, Dark tan, Dark turquoise, Dark violet, Deep cerise, Deep chestnut, Deep fuchsia, Deep lilac, Deep magenta, Deep peach, Deep pink, Denim, Dodger blue, Ecru, Egyptian blue, Electric blue, Electric green (X green), Electric indigo, Electric lime, Electric purple, Emerald, Eggplant, Falu red, Fern green, Firebrick, Flax, Forest green, French Rose, Fuchsia, Fuchsia Pink, Gamboge, Gold (metallic), Gold (web) (Golden), Golden brown, Golden yellow, Goldenrod, Grey-asparagus, Green (color wheel) (X green), Green (HTML/CSS green), Green (pigment), Green (RYB), Green-yellow, Grey, Han Purple, Harlequin, Heliotrope, Hollywood Cerise, Hot Magenta, Hot Pink, Indigo (dye), Indigo (web), International Klein Blue, International orange, Islamic green, Ivory, Jade, Kelly green, Khaki, Khaki (X) (Light khaki), Lavender (floral), Lavender (web), Lavender blue, Lavender blush, Lavender grey, Lavender magenta, Lavender pink, Lavender purple, Lavender rose, Lawn green, Lemon, Lemon chiffon, Light blue, Light pink, Lilac, Lime (color wheel), Lime (web) (X green), Lime green, Linen, Magenta, Magenta (dye), Magenta (process), Magic mint, Magnolia, Malachite, Maroon (HTML/CSS), Maroon (X), Maya blue, Mauve, Mauve Taupe, Medium blue, Medium carmine, Medium lavender magenta, Medium purple, Medium spring green, Midnight Blue, Mint green, Misty rose, Moss green, Mountbatten pink, Mustard, Myrtle, Navajo white, Navy Blue, Ochre, Office green, Old Gold, Old Lace, Old Lavender, Old Rose, Olive, Olive Drab, Olivine, Orange (color wheel), Orange (RYB), Orange (web), Orange Peel, Orange-Red, Orchid, Pale blue, Pale brown, Pale carmine, Pale chestnut, Pale cornflower blue, Pale magenta, Pale pink, Pale red-violet, Papaya whip, Pastel green, Pastel pink, Peach, Peach-orange, Peach-yellow, Pear, Periwinkle, Persian blue, Persian green, Persian indigo, Persian red, Persian pink, Persian rose, Persimmon, Pine Green, Pink, Pink-orange, Platinum, Plum (web), Powder blue (web), Puce, Prussian blue, Psychedelic purple, Pumpkin, Purple (HTML/CSS), Purple (X), Purple Taupe, Raw umber, Razzmatazz, Red, Red (pigment), Red (RYB), Red-violet, Rich carmine, Robin egg blue, Rose, Rose Madder, Rose Taupe, Royal blue, Royal purple, Ruby, Russet, Rust, Safety Orange (Blaze Orange), Saffron, Salmon, Sandy brown, Sangria, Sapphire, Scarlet, School bus yellow, Sea Green, Seashell, Selective yellow, Sepia, Shamrock green, Shocking Pink, Silver, Sky Blue, Slate grey, Smalt (Dark powder blue), Spring bud, Spring green, Steel blue, Tan, Tangerine, Tangerine yellow, Taupe, Tea Green, Tea rose (orange), Tea rose (rose), Teal, Terme (Tawny), Terra cotta, Thistle, Tomato, Turquoise, Tyrian purple, Ultramarine, United Nations blue, Vegas Gold, Vermilion, Violet, Violet (web), Violet (RYE), Viridian, Wheat, White, Wisteria, Yellow, Yellow (process), Yellow (RYB), Yellow-green, and Zinnwaldite, among others.

FIG. 4 shows a perspective view of an embodiment of infant measuring apparatus 10 which includes an infant lying upon on the flexible mat, a portion of which is shown in FIG. 1, between the linear head panel 14 and the linear foot panel 16, and wherein the infant is being cared for by health care personnel.

More specifically, steps for measuring an infant using the infant measuring apparatus 10 are briefly set forth in the text in FIG. 4.

Even more specifically, measurement procedures and illustrations in FIG. 4 are adapted from "How to Weigh and Measure Children", United Nations, New York, 1986, revised 2004, by Irwin J. Shorr, MPH, MPS.

In this respect, following such procedures, the infant measuring apparatus 10 is laid out on a table. The head of the infant is placed in a position along the two-dimensional black central vertical line symbol 37. The feet of the infant are placed to straddle the two-dimensional black vertical central line symbol 37. The linear head panel 14 is perpendicular to the head panel base 18 and is oriented vertically when the head panel base 18 is oriented horizontally when placed on the table. Also, the linear foot panel 16 is perpendicular to the foot panel base 20 and is oriented vertically when the foot panel base 20 is oriented horizontally when placed on the table.

The head of the infant is placed up against the vertically oriented linear head panel 14. The linear foot panel 16 is lifted and excess portions of the flexible mat 12 are passed under the foot panel base 20 so that when the linear foot panel 16 is placed up against the heels of the infant, the foot panel base 20 lies flat on the flexible mat 12.

Reading of the length of the infant is obtained by having the following measurement criteria met. The linear foot panel 16 is oriented perpendicular to the two-dimensional black vertical line symbol 37 on the flexible mat 12. Also, when the inside surface of the linear foot panel 16 contacts the infant's heels, the linear foot panel 16 is aligned in one of the following manners:

a. with a two-dimensional longest blue horizontal line symbol 40 for inch-based measurements, b. with a two-dimensional first-intermediate-length black horizontal line symbols 39 for inch-based measurements, c. with a pair of two-dimensional green diamond symbols 34 for inch-based measurements, d. with a pair of two-dimensional red circle symbols 35 for inch-based measurements, e. with a pair of two-dimensional green diamond symbols 34 and a two-dimensional green horizontal line symbol 33 for inch-based measurements, f. with a pair of two-dimensional red circle symbols 35 and a two-dimensional red horizontal line symbol 36 for inch-based measurements, g. with a pair of two-dimensional shorter blue horizontal line symbols 41 for centimeter-based measurements, h. with a pair of two-dimensional gray horizontal line symbols 43 for centimeter-based measurements, i. with a pair of two-dimensional second-intermediate-length black horizontal line symbols 38 for centimeter-based measurements, or j. with a pair of two-dimensional shortest length black horizontal line symbols 32 for centimeter-based measurements.

When perfect alignment with measuring scale increments is not achieved, then closest approximations are made to existing lines or two-dimensional symbols are made.

Directions for use can be provided in multiple languages, such as English, Spanish, and French.

The material comprising the flexible mat is made from antimicrobial material. More specifically, the flexible mat 12 can be made from PVC sheet manufactured by TSAI-YANG INDUSTRIAL CO., LTD, Republic of China.

Although a wide variety of coloring substances can be employed for providing color coding, for a particular infant measuring apparatus 10, the following specific colors can be employed: the blue color being PMS #2736C; the black color being 100% black; the red color being PMS #485C; the green color being PMS #355C; and the gray color being 30% black.

Figure 5:
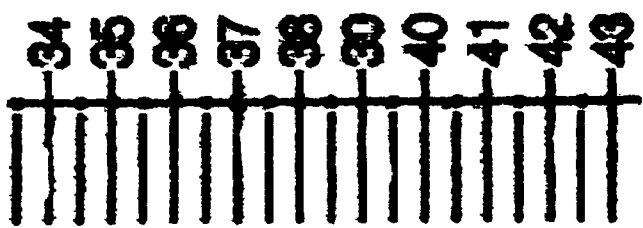
FIG. 5 is a PRIOR ART measuring scale that is used with a Seca Model No. 210 from Seca Corporation.
Figure 5:
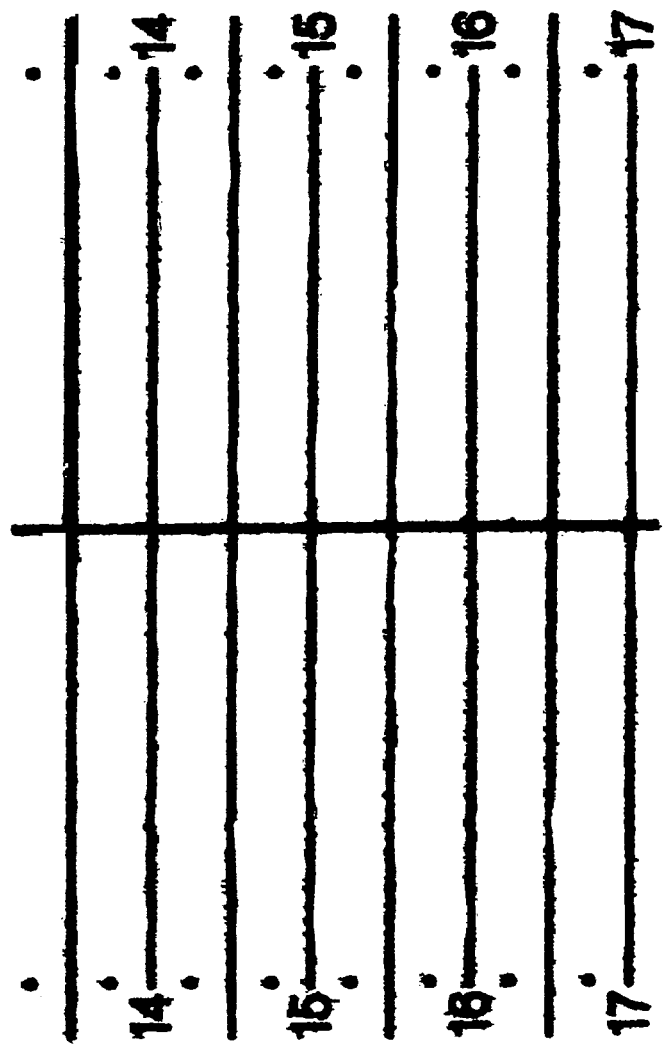
Figure 5:
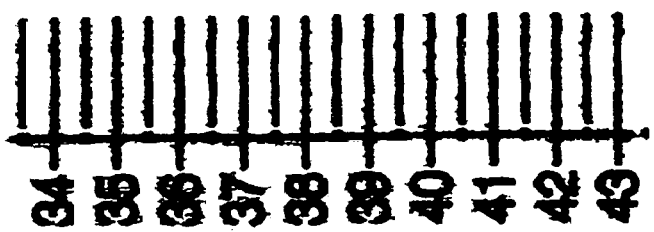

As stated above, FIG. 5 is a PRIOR ART measuring scale that is used with a Seca Model No. 210 from Seca Corporation. More specifically, Seca Model No. 210 is from Seca Corporation, 8920 A Route 108, Columbia, Md. 21045, USA. This item of PRIOR ART has been discussed above.

Figure 7:
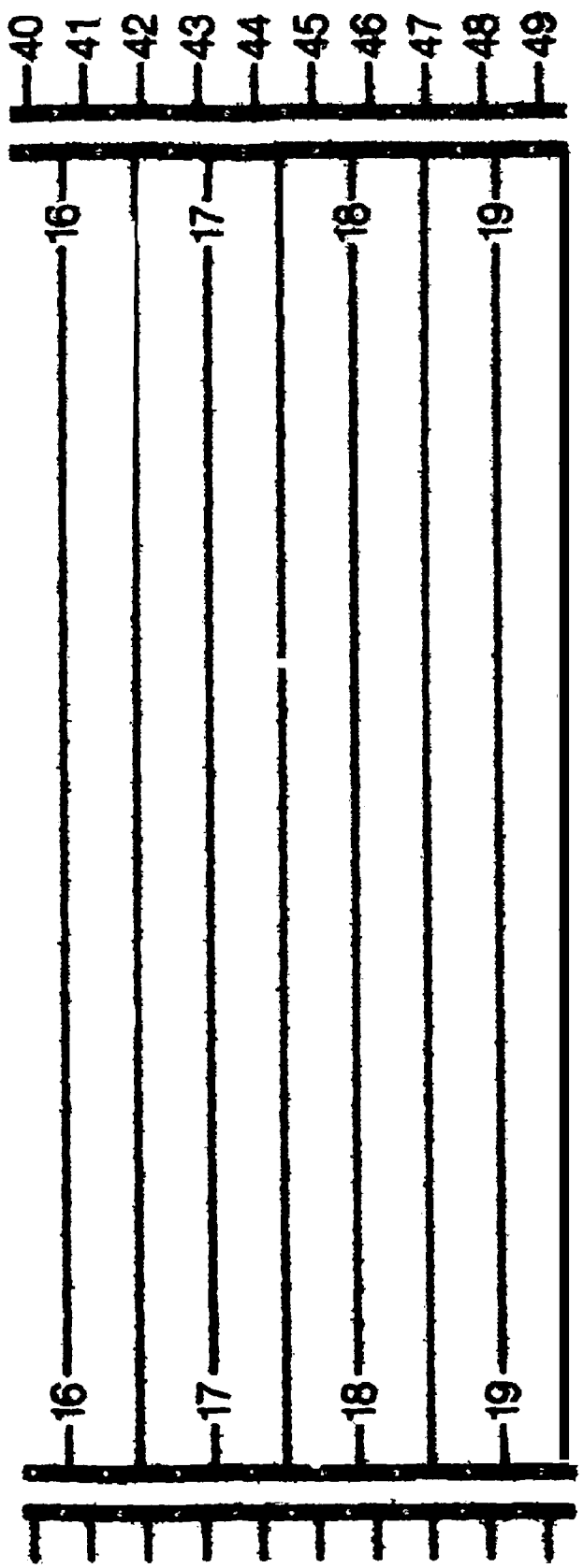
FIG. 7 is a PRIOR ART measuring scale that is used with a Starter's Measure Mat from Slater & Frith LTD.

As stated above, FIG. 7 is a PRIOR ART measuring scale that is used with a Starter's Measure Mat from Slater & Frith LTD. More specifically, Starter's Measure Mat is from Slater & Frith LTD, Lurista House, Stalham Road, Wroxham, Norwich NR128DV, United Kingdom. This item of PRIOR ART has been discussed above.

Figure 6:
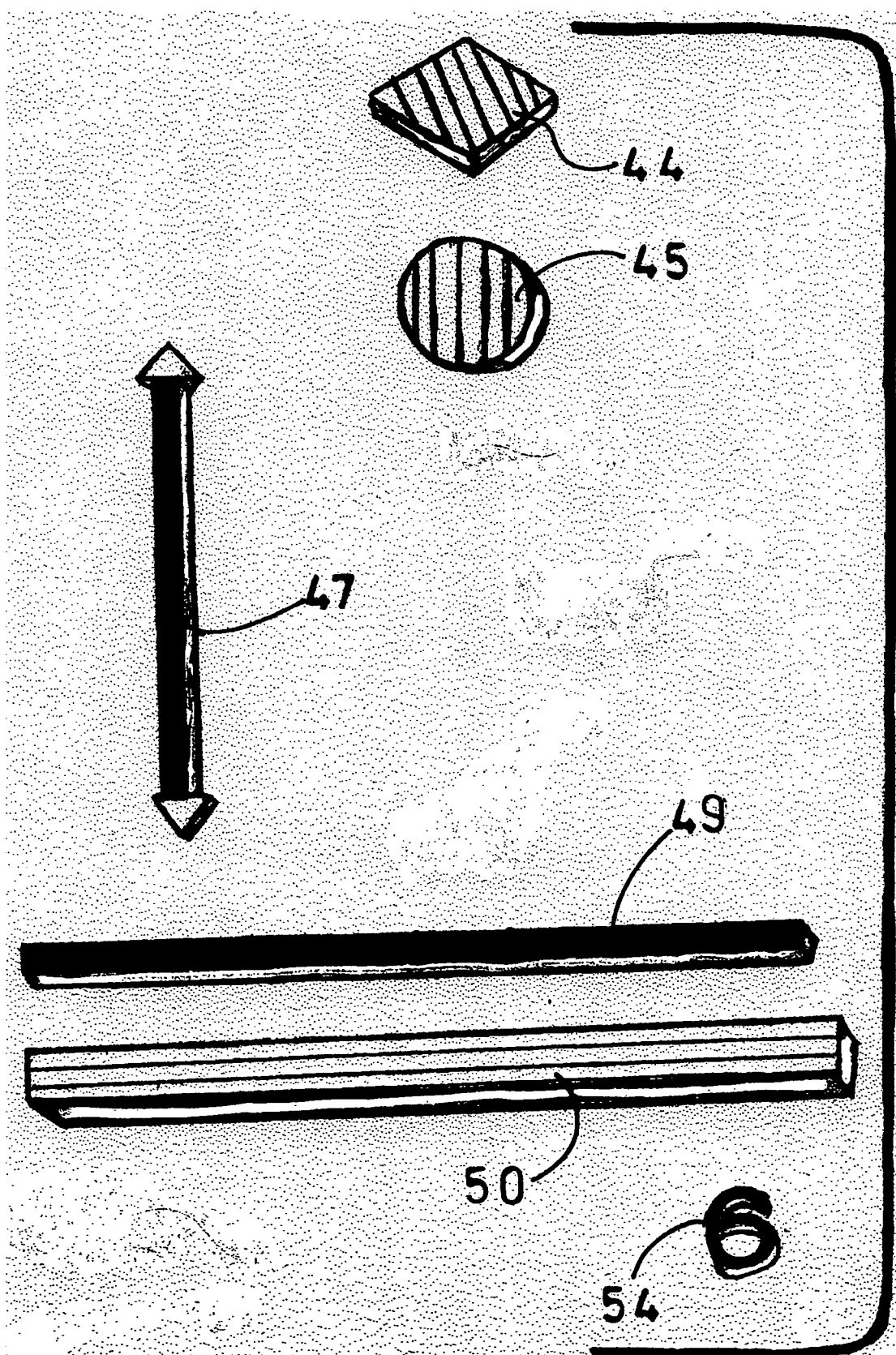
FIG. 6 is a collection of three-dimensional lines and three-dimensional symbols that can be used in an additional embodiment of measuring scale on the flexible mat or on other flat surfaces.

FIG. 6 is a collection of three-dimensional lines and three-dimensional symbols that can be used in an additional embodiment, which is a three-dimensional embodiment of measuring scale on the flexible mat. The three-dimensional embodiment of the invention is shown in detail in FIG. 8.

The three-dimensional embodiment of the invention is especially useful for blind persons and other persons who have limited visual acuity. The three-dimensional embodiment can also be used on a wide variety of other surfaces, especially flat surfaces.

More specifically, the three-dimensional embodiment of the invention includes three-dimensional diamond symbols 44, three-dimensional circle symbols 45, a three-dimensional central vertical line symbol 47, three-dimensional shorter horizontal line symbols 49, three-dimensional longest horizontal line symbols 50, and three-dimensional numerical integer symbols 54. The use of the three-dimensional embodiment of the invention is very similar to the use of related two-dimensional embodiment of the invention described above.

As shown by the color coding in FIG. 6, the three-dimensional embodiment of the invention can also be color coded. That is, the three-dimensional diamond symbols 44 can be green. The three-dimensional circle symbols 45 can be red. The three-dimensional vertical line symbol 47, the three-dimensional shorter horizontal line symbols 49, and the three-dimensional numerical integer symbols 54 can be black. The three-dimensional longest horizontal line symbols 50 can be blue.

Figure 8:
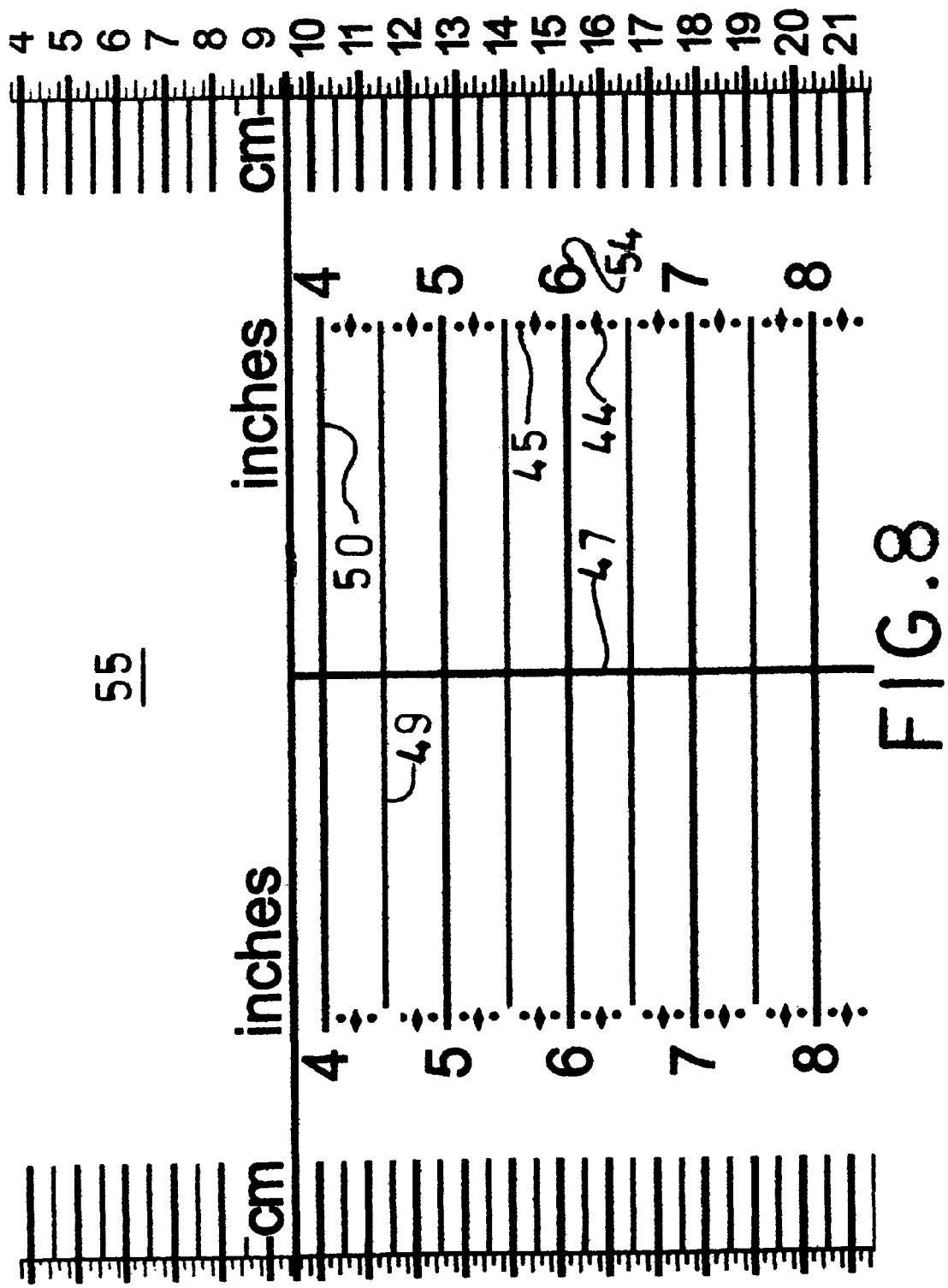
FIG. 8 is a top view of a portion of a second embodiment of the general measuring system of the invention used on a measuring scale on a measuring surface which includes the three-dimensional lines and the three-dimensional symbols shown in FIG. 6.

As stated above, FIG. 8 is a top view of a portion of an additional embodiment of the general measuring system of the invention used on a measuring scale on a measuring surface which includes the three-dimensional lines and the three-dimensional symbols shown in FIG. 6.

More specifically, for an inch-based measuring scale on a measuring surface 55, the subject three-dimensional symbols can include a three-dimensional diamond symbols 44 representing one-quarter inch increments, three-dimensional circle symbols 45 representing one-eighth inch increments, a central three-dimensional vertical line symbol 47 placed as an orientation line, three-dimensional longest horizontal line symbols 50 representing integer increments, three-dimensional shorter horizontal line symbols 49 representing one-half inch increments, and three-dimensional integer symbols 54 representing any actual integer, not just number "6", on the measuring surface 55.

As stated above, the embodiment of the invention shown in FIG. 8 can be especially useful for blind persons. The raised, three-dimensional symbols provide good tactile information for blind persons and other persons having reduced visual acuity. Actually, the raised, three-dimensional symbols can also be used by persons having normal visual acuity in a low ambient light environment.

It is noted that the color coding of the three-dimensional symbols need not be employed for an embodiment of the invention designed for blind persons or other persons having limited visual acuity. It can be used for persons having normal visual acuity to provide tactile aids in conducting measurements.

More specifically, the measuring surface 55 can be any measuring surface. In this respect, the measuring surface 55 can be a second embodiment of a flexible mat used in a variation of the infant measuring apparatus 10.

Furthermore, the three-dimensional symbols can also include three-dimensional symbols which are on a metric measuring scale. More specifically, such a three-dimensional metric measuring scale can include three-dimensional horizontal line symbols (not referenced) that correspond to the two-dimensional shorter blue horizontal line symbols 41 in FIG. 1, three-dimensional horizontal line symbols (not referenced) that correspond to the two-dimensional gray horizontal line symbols 43 in FIG. 1, and three-dimensional horizontal line symbols (not referenced) that correspond to the two-dimensional second-intermediate-length black horizontal line symbols 38 in FIG. 1.

The components of the general measuring system and infant measuring apparatus of the invention can be made from inexpensive and durable plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved general measuring system and infant measuring apparatus that provides a central vertical line on a flexible mat that has a measuring scale on the central vertical line.

With the invention, a general measuring system and infant measuring apparatus is provided which has a measuring system which employs a plurality of line segments of different lengths representing integer measurement increments and fractional measurement increments, where all line segments having the same length are assigned the same respective color in a color coding scheme.

With the invention, a general measuring system and infant measuring apparatus is provided which has a measuring system which employs a plurality of different nonlinear two-dimensional symbols representing different fractional measurement increments, wherein all of the same two-dimensional symbols are assigned the same respective color in the color coding scheme, and wherein different two-dimensional symbols are assigned different colors in the color coding scheme.

With the invention, a general measuring system and infant measuring apparatus is provided which has a measuring system which employs line segments of different lengths which are color coded and different nonlinear two-dimensional symbols which are color coded such that the line segments and the nonlinear two-dimensional symbols which represent the same fractional measurement increments have the same coded color.

With the invention, a general measuring system and infant measuring apparatus is provided which has an inch-based measuring system which employs first nonlinear two-dimensional symbols representing quarter-increments and three-quarter increments which are color coded with one coding color, and second nonlinear two-dimensional symbols representing eighth-increments, three-eighth-increments, five-eighth-increments, and seven-eighth-increments which are color coded with another coding color, wherein the first two-dimensional symbols and the second two-dimensional symbols are not the same two-dimensional symbols.

With the invention, a general measuring system and infant measuring apparatus provides a metric-based measuring system that employs first line segments representing integral-increments, wherein the first line segments have a first line length, a first line thickness, and are color coded with a first coding color, which also employs second line segments representing half-increments, wherein the second line segments have a second line length, a second line thickness, and are color coded with a second coding color, and which also employs third line segments representing nonhalf-fractional-increments, wherein the third line segments have a third line length, a third line thickness, and are color coded with a third coding color.

With the invention, a general measuring system and infant measuring apparatus is provided which has a measuring system that can be very helpful to dyslectic individuals for improving and facilitating measuring accuracy and consistency and can facilitate quicker learning and greater retention.

With the invention, a general measuring system and infant measuring apparatus provides general measuring systems, described herein as desirable in connection with infant measuring apparatuses, which can also be used independently of infant measuring apparatuses in a wide variety of applications such as with tape measures, disposable tapes, rulers, etc.

With the invention, a general measuring system and infant measuring apparatus provides either infant measuring apparatuses or general measuring systems which can be especially useful for blind persons, whereby three-dimensional lines segments and three-dimensional symbols are employed.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

What is claimed is:

1. An infant measuring apparatus, comprising:
   a linear head panel,
   a flexible mat having at top end connected to said linear head panel, and
   a linear foot panel connected to a bottom end of said flexible mat,
   wherein said flexible mat includes thereon a system of linear measurement which includes a first linear scale comprising:
      a plurality of line segments of different lengths representing integer measurement increments and fractional measurement increments, where all line segments having the same length are assigned the same respective color in a color coding scheme, and
      a plurality of different nonlinear two-dimensional symbols representing different fractional measurement increments, wherein all of the same two-dimensional symbols are assigned the same respective color in the color coding scheme, and wherein different two-dimensional symbols are assigned different colors in the color coding scheme.

2. The apparatus of claim 1 wherein:
   said linear head panel is connected to a head panel base, wherein said linear head panel is perpendicular to said head panel base, and
   said linear foot panel is connected to a foot panel base, wherein said linear foot panel is perpendicular to said foot panel base.

3. The apparatus of claim 1 wherein said line segments of different lengths and said different nonlinear two-dimensional symbols are color coded such that line segments and nonlinear two-dimensional symbols which represent the same fractional measurement increment have the same coded color.

4. The apparatus of claim 1 wherein said line segments include:
   first line segments representing integral-increments, wherein said first line segments have a first line length, a first line thickness, and are color coded with a first coding color, and
   second line segments representing half-increments, wherein said second line segments have a second line length, a second line thickness, and are color coded with a second coding color.

5. The apparatus of claim 1 wherein said nonlinear two-dimensional symbols include:
   first nonlinear two-dimensional symbols representing quarter-increments and three-quarter increments which are color coded with a third coding color, and
   second nonlinear two-dimensional symbols representing eighth-increments, three-eighth-increments, five-eighth-increments, and seven-eighth-increments which are color coded with a fourth coding color,
   wherein said first two-dimensional symbols and said second two-dimensional symbols are not the same two-dimensional symbols.

6. The apparatus of claim 1 wherein said system of linear measurement further includes:
   third line segments representing integral-centimeter increments, wherein said third line segments have a third line length, a third line thickness, and are color coded with a fifth coding color,
   fourth line segments representing half-centimeter increments, wherein said fourth line segments have a fourth line length, a fourth line thickness, and are color coded with a sixth coding color, and
   fifth line segments representing nonhalf-centimeter fractional-increments, wherein said fifth line segments have a fifth line length, a fifth line thickness, and are color coded with a seventh coding color.

7. The apparatus of claim 6 wherein said fifth color coding and said first color coding are the same color.

8. The apparatus of claim 6 wherein said fifth color coding and said first color coding are blue.

9. The apparatus of claim 6 wherein said seventh color coding and said second color coding are the same color.

10. The apparatus of claim 6 wherein said seventh color coding and said second color coding are black.

11. The apparatus of claim 1 wherein said flexible mat is made from antimicrobial material.

12. An infant measuring apparatus, comprising:
a linear head panel,
a flexible mat having at top end connected to said linear head panel, and
a linear foot panel connected to a bottom end of said flexible mat,
wherein said flexible mat includes thereon a system of linear measurement which includes a linear scale comprising:
first line segments representing integral-increments, wherein said first line segments have a first line length, a first line thickness, and are color coded with a first coding color,
second line segments representing half-increments, wherein said second line segments have a second line length, a second line thickness, and are color coded with a second coding color, and
third line segments representing nonhalf-fractional-increments, wherein said third line segments have a third line length, a third line thickness, and are color coded with a third coding color.

13. The apparatus of claim 12 wherein:
said first coding color is blue,
said second coding color is gray, and
said third coding color is black.

14. A system of linear measurement which includes a first linear scale comprising:
a plurality of line segments of different lengths representing integer measurement increments and fractional measurement increments, where all line segments having the same length are assigned the same respective color in a color coding scheme, and
a plurality of different nonlinear two-dimensional symbols representing different fractional measurement increments, wherein all of the same two-dimensional symbols are assigned the same respective color in the color coding scheme, and wherein different two-dimensional symbols are assigned different colors in the color coding scheme.

15. The system of linear measurement of claim 14 wherein said line segments of different lengths and said different nonlinear two-dimensional symbols are color coded such that line segments and nonlinear two-dimensional symbols which represent the same fractional measurement increment have the same coded color.

16. The system of linear measurement of claim 14 wherein said line segments include:
first line segments representing integral-increments, wherein said first line segments have a first line length, a first line thickness, and are color coded with a first coding color, and
second line segments representing half-increments, wherein said second line segments have a second line length, a second line thickness, and are color coded with a second coding color.

17. The system of linear measurement of claim 14 wherein said nonlinear two-dimensional symbols include:
first nonlinear two-dimensional symbols representing quarter-increments and three-quarter increments which are color coded with a third coding color, and
second nonlinear two-dimensional symbols representing eighth-increments, three-eighth-increments, five-eighth-increments, and seven-eighth-increments which are color coded with a fourth coding color,
wherein said first two-dimensional symbols and said second two-dimensional symbols are not the same two-dimensional symbols.

18. The system of linear measurement of claim 14, further including a second measurement scale comprising:
third line segments representing integral-metric increments, wherein said third line segments have a third line length, a third line thickness, and are color coded with a fifth coding color,
fourth line segments representing half-metric increments, wherein said fourth line segments have a fourth line length, a fourth line thickness, and are color coded with a sixth coding color, and
fifth line segments representing nonhalf-fractional-metric increments, wherein said fifth line segments have a fifth line length, a fifth line thickness, and are color coded with a seventh coding color.

19. The system of linear measurement of claim 18 wherein said fifth color coding and said first color coding are the same color.

20. The system of linear measurement of claim 18 wherein said fifth color coding and said first color coding are blue.

21. The system of linear measurement of claim 18 wherein said seventh color coding and said second color coding are the same color.

22. The system of linear measurement of claim 18 wherein said seventh color coding and said second color coding are black.

23. A system of metric linear measurement which includes a linear scale comprising:
first line segments representing integral-metric increments, wherein said first line segments have a first line length, a first line thickness, and are color coded with a first coding color,
second line segments representing half-metric increments, wherein said second line segments have a second line length, a second line thickness, and are color coded with a second coding color, and
third line segments representing nonhalf-fractional-metric increments, wherein said third line segments have a third line length, a third line thickness, and are color coded with a third coding color.

24. The system of linear measurement of claim 23 wherein:
said first coding color is blue,
said second coding color is gray, and
said third coding color is black.

25. A system of linear measurement which includes a three-dimensional linear scale comprising:
a plurality of three-dimensional line segments of different lengths representing integer measurement increments and fractional measurement increments,
a plurality of different nonlinear three-dimensional symbols representing different fractional measurement increments, and
a plurality of three-dimensional numerical integer symbols.

26. The system of linear measurement of claim 25 wherein said three-dimensional line segments include:
first three-dimensional line segments representing integral-increments, wherein said first line segments have a first line length, and a first line thickness, and
second three-dimensional line segments representing half-increments, wherein said second line segments have a second line length, and a second line thickness.

27. The system of linear measurement of claim 25 wherein said nonlinear three-dimensional symbols include:
    first nonlinear three-dimensional symbols representing quarter-increments and three-quarter increments, and
    second nonlinear three-dimensional symbols representing eighth-increments, three-eighth-increments, five-eighth-increments, and seven-eighth-increments,
    wherein said first three-dimensional symbols and said second three-dimensional symbols are not the same three-dimensional symbols.

\* \* \* \* \*